United States Patent [19]

Chan et al.

[11] Patent Number: 5,446,041
[45] Date of Patent: Aug. 29, 1995

[54] INTRAOCULAR PRESSURE REDUCING 11-ACYL PROSTAGLANDINS

[75] Inventors: Ming F. Chan, Santa Ana; David F. Woodward, El Toro, both of Calif.

[73] Assignee: Allergan, Inc., Irvine, Calif.

[21] Appl. No.: 596,430

[22] Filed: Oct. 10, 1990

Related U.S. Application Data

[63] Continuation of Ser. No. 386,835, Jul. 27, 1989, abandoned.

[51] Int. Cl.$^6$ ............... A61K 31/215; A61K 31/23; A61K 31/22
[52] U.S. Cl. .................. 514/530; 514/546; 514/549; 514/552; 514/913
[58] Field of Search ............ 514/530, 546, 549, 552, 514/913

[56] References Cited

U.S. PATENT DOCUMENTS

| 4,001,306 | 1/1977 | Morozowich et al. | 260/472 |
| 4,060,540 | 11/1977 | Bernady et al. | 556/441 |
| 4,822,819 | 4/1989 | DeSantis et al. | 514/530 |
| 4,824,857 | 4/1989 | Goh et al. | 514/398 |
| 4,883,819 | 11/1989 | Bito II | 514/573 |

FOREIGN PATENT DOCUMENTS

| 0172963 | 3/1986 | European Pat. Off. |
| 0286903 | 4/1987 | European Pat. Off. |
| 2357781 | 5/1974 | Germany |
| 8806448 | 9/1988 | WIPO |
| 8903384 | 4/1989 | WIPO |

OTHER PUBLICATIONS

Starr, *Exp. Eye Res.* 11, 170–177 (1971).
Zajacz et al., *The Eye: Reproduction, Obstetrics and Gynecology* 4, 316 (1976).
Keun Kim *Investigative Ophthalmology* 14, 36 (1975).
Camras et al., *Invest. Ophthalmol. Visual Sci.* 16, 1125 (1977).
Woodward et al., *Invest. Ophthalmol. Visual Sci.* 30, 1838 (1989).
Nilsson et al., *Exp. Eye Res.* 48, 707 (1989).
Bito, *Arch. Ophthalmol.* 105, 1036 (1987).
Siebold et al., *Prodrug* 5, 3 (1989).
Carmely, S. and Kashman, Y., *Tetrahedron Letters* 21:875–878 (1980).

Primary Examiner—Frederick E. Waddell
Assistant Examiner—Zohreh A. Fay
Attorney, Agent, or Firm—Robert J. Baran; Martin A. Voet; Howard R. Lambert

[57] ABSTRACT

Disclosed is an intraocular pressure reducing method and composition wherein 11-acyl prostaglandins are contained in a pharmaceutically acceptable excipient for topical application to the surface of the eye.

14 Claims, No Drawings

INTRAOCULAR PRESSURE REDUCING 11-ACYL PROSTAGLANDINS

This application is a continuation of application Ser. No. 386,835, filed 27 Jul. 1989, now abandoned.

BACKGROUND OF THE INVENTION

The present invention relates to a means for reducing or maintaining intraocular pressure. More particularly it relates to a method and composition for reducing or maintaining intraocular pressure involving the administration of a composition containing an 11-acyl prostaglandin in an ophthalmically acceptable carrier.

The method and compositions of the present invention are particularly useful for the management of glaucoma, a disease of the eye characterized by increased intraocular pressure. On the basis of its etiology, glaucoma has been classified as primary or secondary. For example, primary glaucoma in adults, congenital glaucoma, may be either chronic open-angle or acute or chronic angle-closure. Secondary glaucoma results from pre-existing ocular diseases such as uveitis, intraocular tumor or an enlarged cataract.

The underlying causes of primary glaucoma are not yet well known. The increased intraocular tension is due to obstruction of aqueous humor outflow. In chronic open-angle glaucoma, the anterior chamber and its anatomic structures appear normal, but drainage of the aqueous humor is impeded. In acute and chronic angle-closure glaucoma, the anterior chamber is shallow, the filtration angle is narrowed and the iris may obstruct the trabecular meshwork at the entrance to the canal of Schlemm. Dilation of the pupil may push the root of the iris forward against the angle or may produce pupillary block and thus precipitate an acute attack. Eyes with narrow anterior chamber angles are predisposed to acute angle-closure glaucoma attacks of varying degrees of severity.

Secondary glaucoma is caused by any interference with the flow of aqueous humor from the posterior chamber into the anterior chamber and subsequently, into the canal of Schlemm. Inflammatory disease of the anterior segment may prevent aqueous escape by causing complete posterior synechia in iris bombe, and may plug the drainage channel with exudates. Other common causes are intraocular tumors, enlarged cataracts, central retinal vein occlusion, trauma to the eye, operative procedures and intraocular hemorrhage.

Considering all types together, glaucoma occurs in about 2% of all persons over the age of 40 and may be asymptomatic for years before progressing to rapid loss of vision. In cases where surgery is not indicated, topical $\beta$-adrenoceptor antagonists have traditionally been the drugs of choice for treating glaucoma.

Carbon-1 esters of certain prostaglandins have been reported to possess ocular hypotensive activity. However, prostaglandin ocular hypotensives generally suffer from the disadvantage of inducing conjunctival hyperemia of varying severity and duration, smarting, and foreign body sensation, as well as presenting solubility problems in certain ophthalmically advantageous carriers.

This invention relates to derivatives of the known prostaglandins formulated in a pharmaceutically acceptable vehicle, and ophthalmic use of those prostaglandins. The present invention has numerous advantages over the prior art, including increased duration of action and reduction of the aforementioned undesirable side effects, along with being easily solubilized in certain ophthalmically advantageous carriers.

SUMMARY OF THE INVENTION

In accordance with one aspect of the present invention, there is provided a method of treating ocular hypertension which comprises applying to the eye an amount sufficient to treat ocular hypertension of an 11-acyl compound of formula I.

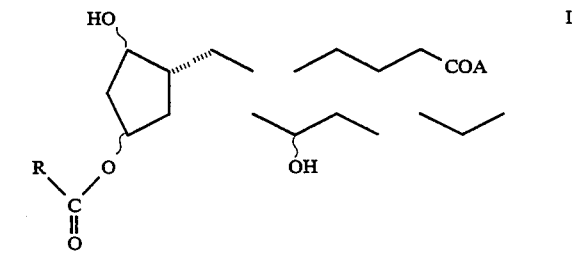

In formula I, the hydroxyl groups are in either the $\alpha$ or $\beta$ configuration; the dashed bonds at C-5, C-13 and C-17 represent either a single bond, or a double bond which can be in the cis or trans configuration; A is —OH, O⁻X⁺ where X⁺ is a pharmaceutically acceptable cation or —OR$_1$ where R$_1$ is alkyl of 1 to 6 carbon atoms; R is an acyclic hydrocarbon, saturated or unsaturated, having from 1 to 20 carbon atoms, or R is —(CH$_2$)$_n$R$_2$ where n is 0–10 and R$_2$ is an aliphatic ring or an aromatic or heteroaromatic ring.

In accordance with another aspect of the present invention, there is provided an ophthalmically acceptable composition for reducing ocular hypertension which comprises at least one 11-acyl prostaglandin described above, present in a ophthalmically acceptable excipient for topical application to the surface of the eye. Such an excipient is one which does not have a deleterious or untoward effect on the eye when used in normal treatment regimens.

Further features and advantages of the present invention will become apparent from the detailed description of preferred embodiments which follows, taken together with the examples and claims appended hereto.

DETAILED DESCRIPTION OF PREFERRED EMBODIMENTS

It has been discovered that certain prostaglandins lower intraocular pressure in man and other mammals when applied topically to the eye. Although the precise mechanism is not yet known, prostaglandins appear to increase aqueous humor outflow to restore a normotensive or hypotensive state. However, topical application of prostaglandins generally causes side effects such as conjunctival hyperemia, smarting and foreign body sensation which range in degree from undesirable to unacceptable, depending upon the particular patient and dosage necessary to produce a sufficient pressure regulating effect.

In accordance with one aspect of the present invention, there has been provided a method for treating ocular hypertension which comprises administering to the eye a compound of formula I. It has further been discovered that these esters are more effective than PGF$_{2\alpha}$ both in terms of degree and duration of activity. In addition, animals treated with formulations comprising these 11-acyl prostaglandins experience reduced adverse side effects, notably ocular surface hyperemia.

In the foregoing illustration, as well as those provided hereinafter, wavy line attachments indicate either the alpha (α) or beta (β) configuration. The dotted lines on bonds between carbons 5 and 6 (C-5), between carbons 13 and 14 (C-13), and between carbons 17 and 18 (C-17) indicate a single or double bond which can be in the cis or trans configuration. If two solid lines are used at C-5, C-13, or C-17, it indicates a specific configuration for that double bond. Hatched lines used at position C-9, C-11 and C-15 indicate the α configuration. If one were to draw the β configuration, a solid triangular line would be used at either of these three positions.

The naturally occurring stereochemistry of PGF$_{2\alpha}$ includes the C-9, C-11 and C-15 hydroxyl groups in the α configuration. In the compositions of the present invention, however, esters of prostaglandins having the C-9 or C-11 or C-15 hydroxyl group in the β configuration are also contemplated. In addition to configurational variations, the substituent group at each of the 9 and 11 positions may be varied.

The 11-acyl prostaglandins suitable for use in this invention can comprise any of a variety of acyl substituents at the 11 position. As per formulas I, R can be an aliphatic hydrocarbon having from one to twenty carbon atoms, inclusive. Preferably R has from one to ten carbon atoms, particularly methyl, ethyl, propyl, butyl or pentyl, or an isomeric form thereof. Most preferably R is —CH$_3$, —(CH$_2$)$_3$CH$_3$, —CH(CH$_3$)$_2$ or —C(CH$_3$)$_3$.

Alternatively R can comprise a cyclic component. In particular, R can be (CH$_2$)$_n$R$_2$ where n is 0–10 and R$_2$ is a saturated or unsaturated ring, perferably a saturated ring, having from three to seven carbon atoms, inclusive, or an aromatic or heteroaromatic ring, preferably one having 5 to 7 carbon atoms, and having oxygen, nitrogen or sulfur in the case of a heteroaromatic ring. Preferably the aliphatic, aromatic or heteroaromatic ring will have 5 or 6 carbon atoms. Preferably n is 0–4.

The Preferred compounds of this invention are those which have the following structures.

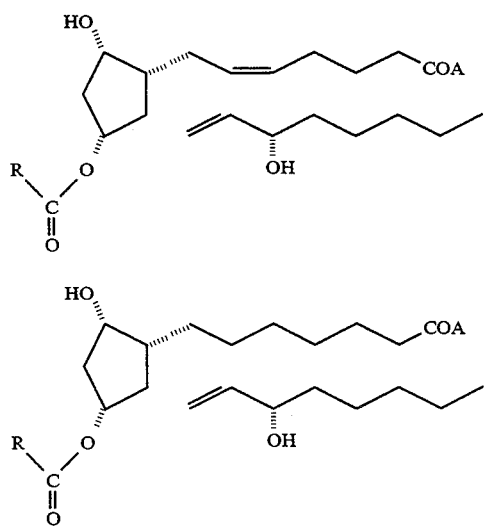

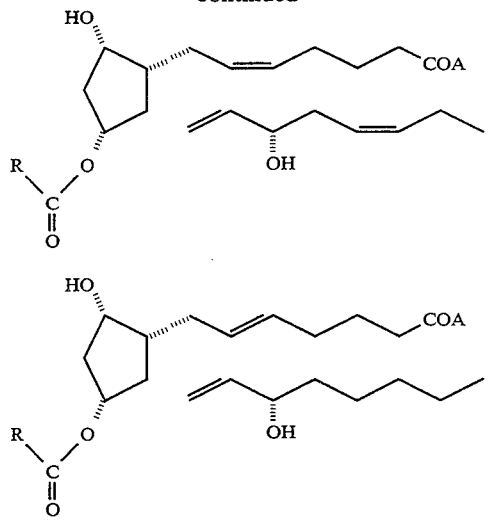

These several most prefered structures will have as the preferred individual substituents, those substituents recited above in the several paragraphs noting same.

Where A is —OH the acid can be converted to a salt O−X+ where X$^{30}$ is the anion component of any of a variety of pharmaceutically acceptable salts. A pharmaceutically acceptable salt may be prepared for any compound in this disclosure having a functionality capable of forming such salt, in particular, the carboxylic acid group at C-1 of the prostaglandins disclosed herein. A pharmaceutically acceptable salt is any salt which retains the activity of the parent compound and does not impart any deleterious or undesirable effect on the subject to whom it is administered and in the context in which it is administered.

A pharmaceutically acceptable salt of an acid may be derived from an organic or inorganic base. Such a salt may be a mono- or polyvalent ion. Of particular interest are the inorganic ions, sodium, potassium, calcium, magnesium and zinc. Organic ammonium salts may be made with amines, such as mono-, di-, and trialkyl amines or ethanolamines. Salts may also be formed with caffeine, tromethamine and similar molecules.

In another aspect, this invention relates to a composition which can be applied topically to the eye to lower intraocular pressure. This composition comprises one or more of the foregoing 11-acyl prostaglandins therein. The composition may comprise any of a variety of ophthalmically acceptable carriers as will be known to those skilled in the art of ocular drug delivery. A preferred method of application would be topical, in a pharmaceutically acceptable topical formulation. Such a carrier may be comprised of a saline and/or detergent, containing pharmaceutically required or advantageous adjuvants, along with an effective dose of the intraocular pressure reducing drug.

In accordance with a preferred embodiment of the present invention, the carrier comprises a solution having polysorbate 80–10 mM TRIS in the range of from about 0.05–1.0% by weight, and preferably about 0.1%, which is particularly suited for administration in the form of a liquid eye drop. This carrier may additionally comprise pharmaceutically advantageous adjuvants such as a preservative, antibiotic/antimycotic agents, pH buffers or osmotic balancers.

The optimal concentration of the prostaglandin derivative is a function of a variety of factors, such as desired frequency of application and duration of effect, level of adverse side effects and considerations implicated by the chemical nature of the carrier. In general, however, concentrations are contemplated within the range of from about 0.0001% to 1%, preferably from 0.001% to 0.1% by weight in relation to the pharmaceutically acceptable carrier.

Further features and advantages of the present invention will become apparent from the detailed description of preferred embodiments which follows, taken together with the examples and claims appended hereto.

The acylation reaction for producing the foregoing 11-acyl compounds is illustrated in the Examples or is known to those skilled in the synthetic organic chemical arts.

The invention can be more fully understood by the following examples. All temperatures are in degrees centigrade.

EXAMPLE 1

Preparation of 11-Pivaloyl $PGF_{2\alpha}$

Prostaglandin $F_{2\alpha}$ (from Chinoin Chemical Co., 70.0 mg, 0.197 mmol) was suspended in methylene chloride (2 ml) and cooled in an ice bath. A solution of diazomethane in ether was added dropwise to the above suspension until a yellow color persisted. The solution was stirred at 25° C. for 30 min and the solvents were evaporated to give the $PGF_{2\alpha}$ methyl ester.

$^1$HNMR (300 MHz, $CDCl_3$): δ5.3–5.6 (4H, m), 4.16 (1H, br s), 4.06 (1H, q, J=6.51 Hz), 3.93 (1H, br s), 3.67 (3H, s), 2.70 (1H, br s), 2.32 (2H, t, J=7.3 Hz), 1.2–2.4 (21H, m) and 0.88 ppm (3H, distorted t, J=6Hz).

The crude methyl ester from above was heated under reflux with butylboronic acid (24 mg, 0.236 mmol) in methylene chloride (0.4 ml) for 30 minutes. The solvent was removed under reduced pressure and replaced with dry benzene. The benzene was again evaporated under reduced pressure. This process was repeated twice to remove traces of water by azeotropic distillation. The crude boronate (89 mg, 0.197 mmol) was dissolved in dry dichloromethane (0.7 ml) and cooled to 0° C. in an ice bath. 2,6-Lutidine (57 μl, 0.49 mmol) and t-butyldimethylsilyl trifluoromethanesulfonate (90 μl, 0.39 mmol) were added and the reaction was stirred at 25° C. for 16 hours. The reaction mixture was diluted with ethyl acetate (15 ml) and washed with 10% citric acid and brine. After drying over magnesium sulfate and evaporation of solvents, a crude product was obtained which was stirred in methanol (2 ml) at 25° C. for 2 hours. After one change of methanol, the solvents were evaporated to give crude $PGF_{2\alpha}$ methyl ester 15-t-butyldimethylsilyl ether. Purification by flash chromatography (silica gel, 40% ethyl acetate in hexanes, $R_f$ 0.24) gave the purified product.

Purified $PGF_{2\alpha}$ methyl ester 15-t-butyldimethylsilyl ether (43 mg) was dissolved in dry pyridine (0.4 ml) and cooled in an ice bath for approximately 10 min. Trimethylacetyl chloride (29 μl, 0.236 mmol) was added and the reaction was stirred at 0° C. for 10 min before storing in a 2° C. refrigerator overnight (14 hours). The solvent and volatiles were evaporated in vacuo and the residue was partitioned between 10% citric acid and ethyl acetate. The aqueous layer was extracted three times with ethyl acetate and the combined organic extract was washed with brine and dried over magnesium sulfate. The organic layer was concentrated to give 130 mg crude product. Purification was achieved by TLC (1 mm silica gel plate, 25% ethyl acetate in hexanes, $R_f$ 0.04), giving the 11-pivaloyl $PGF_{2\alpha}$ methyl ester 15-t-butyldimethylsilyl ether.

The foregoing product was dissolved in tetrahydrofuran (0.57 ml) and 0.5N lithium hydroxide (560 μl, 0.28 mmol) was added. The two-phase mixture was vigorously stirred at 25° C. until the starting material was totally consumed (18 hours). The reaction mixture was cooled to 0° C., acidified with 10% citric acid and extracted with ethyl acetate (3×7 ml). The organic extract was washed with brine, dried over magnesium sulfate and concentrated. The crude was purified to give the 11-pivalolyl $PGF_{2\alpha}$ 15-t-butyldimethylsilyl ether.

This product (22 mg, 0.039 mmol) was stirred in a mixture of acetic acid (214 μl) and water (54 μl) at 25° C. for 48 hours. The solvents were evaporated in vacuo and the residue was chromatographed (silica gel, 40% ethyl acetate in hexanes $R_f$0.45) to give the 11-pivalolyl $PGF_{2\alpha}$.

$^1$H NMR (300 MHz, $CDCl_3$): δ5.3–5.6 (4H, m), 4.8–4.9 (1H, m), 4.1–4.25 (2H, m), 2.0–2.55 (6H, m), 2.30 (2H, t, J=7 Hz), 1.0–1.8 (12H, m), 1.14 (9H, s) and 0.85 ppm (3H, distorted t, J=6 Hz).

Proceeding in a similar manner the other 11-acyl prostaglandins of this invention can be made, paricularly the 11-acetyl, 11-isobutyryl, 11-valeryl,and the 11-isovaleryl compounds.

EXAMPLE 2

Intraocular Pressure Reducing Effect in Rabbits

Starting with $PGF_{2\alpha}$, experimental quantities of the 11-isobutyryl and 11-pivaloyl derivatives were prepared in accordance with the procedure of Example 1. The resulting 11-acyl $PGF_{2\alpha}$ compounds were added to a polysorbate carrier in amounts to produce a 0.01%, 0.1% and 1% solution of each ester. A group of 8 experimental rabbits was treated by administering approximately one drop of each solution to the surface of the eye, and intraocular pressure was measured by applanation pneumatonometry (Model 30 RT manufactured by Digilab) at the time of administration and at intervals of 2, 3, 4, 6, 8 and 10 hours thereafter. Ocular surface hyperemia was also scored at these intervals. The following data were obtained.

TABLE I

| INTRAOCULAR PRESSURE AND OCULAR SURFACE HYPEREMIA CHANGES AT PREDETERMINED TIMES (HR) AFTER PROSTAGLANDIN ADMINISTRATION |||||||||
|---|---|---|---|---|---|---|---|
| | | Time (Hours) ||||||
| Compound | PG Dose % | 2 | 3 | 4 | 6 | 8 | 10 |
| | | Reduction in IOP ||||||
| $PGF_{2\alpha}$ | 0.01% | 0.4 | 2.3[1] | 1.3 | 0.25 | — | — |
| | 0.1% | 2.4 | 6.1[1] | 3.9[2] | 2.2[1] | −1.1 | — |

TABLE I-continued

INTRAOCULAR PRESSURE AND OCULAR SURFACE HYPEREMIA CHANGES AT PREDETERMINED TIMES (HR) AFTER PROSTAGLANDIN ADMINISTRATION

| Compound | PG Dose % | Time (Hours) | | | | | |
|---|---|---|---|---|---|---|---|
| | | 2 | 3 | 4 | 6 | 8 | 10 |
| | 1.0% | 1.2 | 7.2[1] | 7.0[1] | 10.3[1] | — | — |
| 11-isobutyryl $PGF_{2\alpha}$ | 0.01% | 2.1[1] | 0.075 | 2.6 | 1.1 | — | — |
| | 0.1% | — | 0.3 | 4.1[2] | 4.9[1] | 5.3[1] | 4.7[1] |
| | 1.0% | — | 1.4 | 3.4[2] | 11.2[1] | — | — |
| 11-pivaloyl $PGF_{2\alpha}$ | 0.01% | 6.9[1] | — | 5.1[1] | 3.2[1] | 1.6[2] | 0.5 |
| | 0.1% | 3.4 | — | 10.5[1] | 12.5[1] | 10.5[1] | 11.6[1] |
| | 1.0% | — | — | 0.1 | 12.2[1] | 13.2[1] | 14.3[1] |
| Percent Animal Exhibiting Ocular Surface Hyperemia | | | | | | | |
| $PGF_{2\alpha}$ | 0.01% | 100 | 100 | 50 | 12 | — | — |
| | 0.1% | 100 | 100 | 100 | 75 | 0 | — |
| | 1.0% | 100 | 100 | 100 | 100 | — | — |
| 11-isobutyryl $PGF_{2\alpha}$ | 0.01% | 50 | 25 | 12.5 | 12.5 | — | — |
| | 0.1% | 100 | 100 | 100 | 75 | 37 | 37 |
| | 1.0% | 100 | 100 | 100 | 100 | — | — |
| 11-pivaloyl $PGF_{2\alpha}$ | 0.01% | 100 | — | 75 | 25 | 0 | 0 |
| | 0.1% | 100 | — | 100 | 50 | 0 | 0 |
| | 1.0 | 33 | — | 33 | 33 | 13 | 0 |

[1]$p < 0.01$;
[2]$p < 0.05$.

Comparison of the intraocular pressure effects of the 11-acyl $PGF_{2\alpha}$ derivatives with the parent compond reveals a distinct increase in both the degree and duration of ocular hypotensive activity. Moreover, 11-acyl $PGF_{2\alpha}$ esters cause pronounced decreases in intraocular pressure with a marked reduction in the incidence of ocular surface hyperemia. In the case of $PGF_{2\alpha}$, ocular hypotensive activity is achieved only with a very high incidence of ocular surface hyperemia. The beneficial effects of the 11-acyl PGF2α derivatives compared to the parent compound may be readily appreciated by comparing the relative activities at the 0.1% dose. $PGF_{2\alpha}$ (0.1%) caused a maximum decrease in intraocular pressure at 3 hours (6.1 mm Hg) with a significant reduction in IOP lasting for only 4 hours and a 100% incidence of hyperemia at 3 and 4 hours. In contrast, 11-isobutyryl $PGF_{2\alpha}$ caused an appromximately 5 mm Hg decrease in intraocular pressure which persisted for 10 hours with only a 37% incidence of hyperemia at the 8 and 10 hour time points. The 11-pivaloyl $PGF_{2\alpha}$ was even more potent and caused a greater than10 mm Hg decrease in IOP at 8 and 10 hours with no associated ocular surface hyperemia.

These examples have been set out to illustrate, but not limit, the scope of the invention.

What is claimed:

1. A method of treating ocular hypertension which comprises applying to the eye in an ophthalmically acceptable excipient an amount sufficient to treat ocular hypertension of the compound:

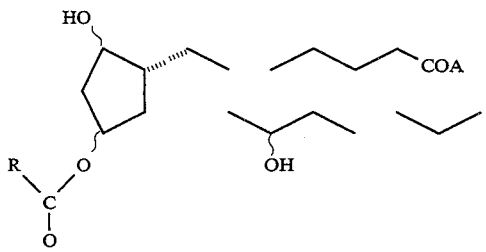

where the hydroxyl groups are in either the α or β configuration; the dashed bonds at C-5, C-13 and C-17 represent either a single bond, or a double bond which can be in the cis or trans configuration; A is —OH, or a pharmaceutically acceptable salt thereof or —$OR_1$ where $R_1$ is alkyl of 1 to 6 carbon atoms; R is an acyclic hydrocarbon, saturated or unsaturated, having from 1 to 20 carbon atoms, or R is —$(CH_2)_nR_2$ where n is 0–10 and $R_2$ is an aliphatic ring or an aromatic ring.

2. The method of claim 1 where the C-5 and C-13 bonds are cis and trans double bonds respectively and the C-17 bond is a single bond, the compound having the following formula:

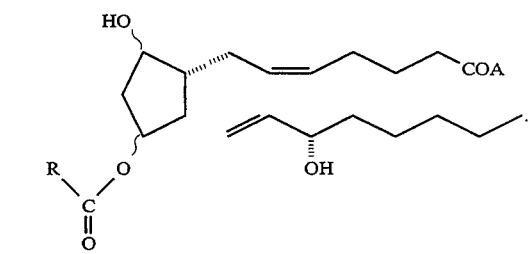

3. The method of claim 2 wherein R is methyl, ethyl, propyl, butyl, or pentyl, or an isomeric form thereof.

4. The method of claim 3 where the C-9, C-11 and C-15 substituents are in the α configuration, the compound of the following formula:

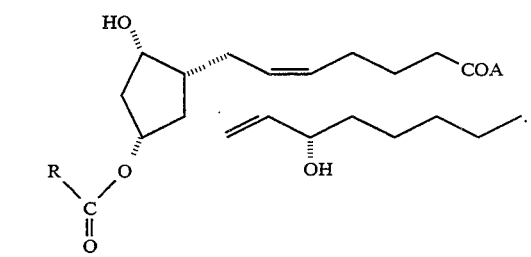

5. The method of claim 4 where R is —$CH_3$, —$(CH_2)_3CH_3$, —$CH(CH_3)_2$ or —$C(CH_3)_3$.

6. The method of claim 1 where the C-5 and C-13 bonds are trans double bonds, C-17 is a single bond and each of the C-9, C-11 and C-15 substituents are in the G configuration, the compound having the following structure:

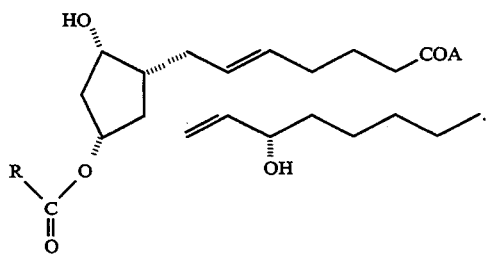

7. The method of claim 6 where R is methyl, ethyl, propyl, butyl, or pentyl, or an isomeric form thereof.

8. The method of claim 7 where R is —CH$_3$, —CH(CH$_3$)$_2$, or —C(CH$_3$)$_3$.

9. The method of claim 1 where the compound is a 11-acyl PGF$_{3\alpha}$ derivative of the following formula:

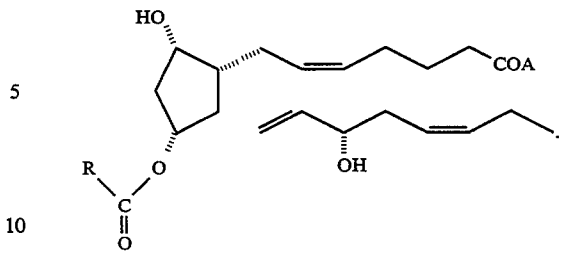

10. The method of claim 9 where R is methyl, ethyl, propyl, butyl, or pentyl, or an isomeric form thereof.

11. The method of claim 10 where R is —CH$_3$, —CH(CH$_3$)$_2$, or —C(CH$_3$)$_3$.

12. The method of claim 1 where the compound is the 11-acyl derivative of PGF$_{1\alpha}$, the compound of the following formula:

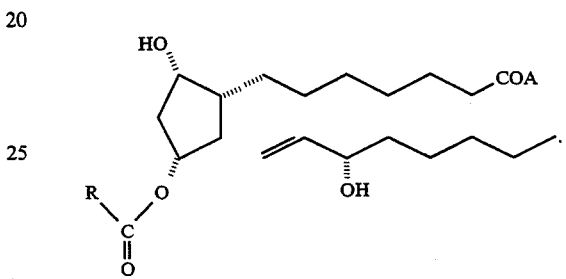

13. The method of claim 12 where the R group of that compound is methyl, ethyl, propyl, butyl, or pentyl, or an isomeric form thereof.

14. The method of claim 13 where R is —CH$_3$, —CH(CH$_3$)$_2$, or —C(CH$_3$)$_3$.

* * * * *

UNITED STATES PATENT AND TRADEMARK OFFICE
CERTIFICATE OF CORRECTION

PATENT NO. : 5,446,041
DATED : Aug. 29, 1995
INVENTOR(S) : Chan et al

Page 1 of 4

It is certified that error appears in the above-indentified patent and that said Letters Patent is hereby corrected as shown below:

Column 2, line 11; delete formula and insert in place thereof

-- 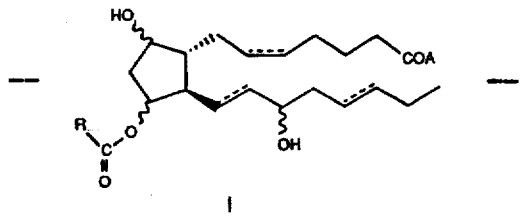 --

Column 3, lines 47-67; delete formulas and insert in place thereof

-- 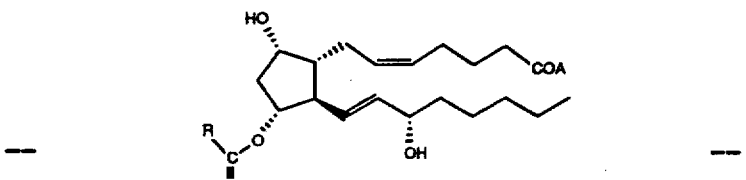 --

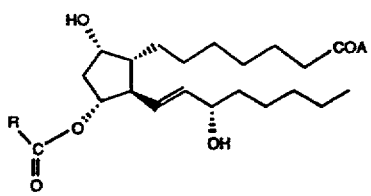

UNITED STATES PATENT AND TRADEMARK OFFICE
CERTIFICATE OF CORRECTION

PATENT NO. : 5,446,041
DATED : Aug. 29, 1995
INVENTOR(S) : Chan et al

It is certified that error appears in the above-indentified patent and that said Letters Patent is hereby corrected as shown below:

Column 4, lines 1-22; delete formulas and insert in place thereof

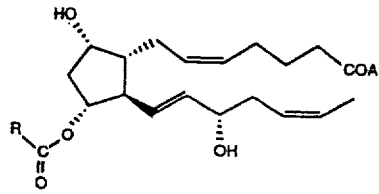

--

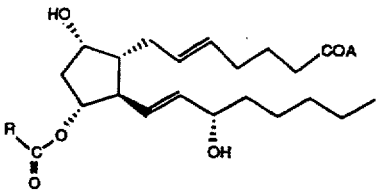

--

Column 4, line 27; delete "$X^{30}$" and insert in place thereof --$X^+$--
Column 7, line 21; delete "$^1p$" and insert in place thereof --1-p--
Column 7, line 22; delete "$^2p$" and insert in place thereof --2-p--
Column 7, line 55 (claim 1); delete formula and insert in place thereof --  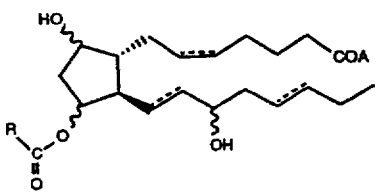  --

UNITED STATES PATENT AND TRADEMARK OFFICE
CERTIFICATE OF CORRECTION

PATENT NO. : 5,446,041
DATED : Aug. 29, 1995
INVENTOR(S) : Chan et al

Page 3 of 4

It is certified that error appears in the above-indentified patent and that said Letters Patent is hereby corrected as shown below:

Column 8, line 36 (claim 2); delete formula and insert in place thereof

-- 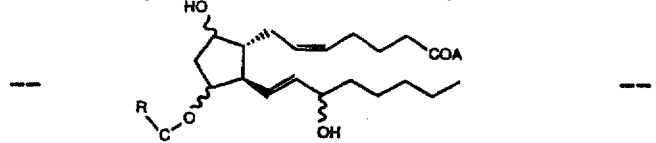 --

Column 8, line 54 (claim 4); delete formula and insert in place thereof

-- 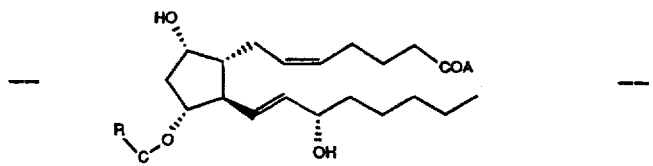 --

Column 8, line 68 (claim 6); delete "G" and insert in place thereof --$\alpha$--
Column 9, line 10 (claim 6); delete formula and insert in place thereof -- 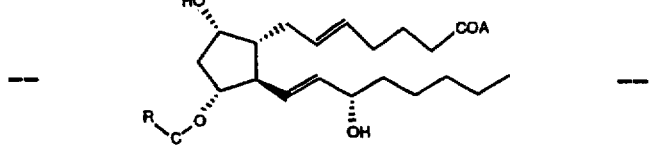 --

Column 10, line 1; delete formula and insert in place thereof (claim 9)

-- 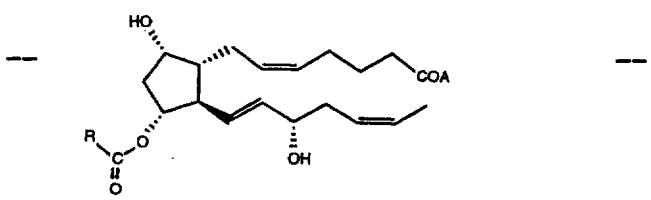 --

UNITED STATES PATENT AND TRADEMARK OFFICE
CERTIFICATE OF CORRECTION

PATENT NO. : 5,446,041
DATED : Aug. 29, 1995
INVENTOR(S) : Chan et al

It is certified that error appears in the above-indentified patent and that said Letters Patent is hereby corrected as shown below:

Column 10, line 20 (Claim 12); delete formula and insert in place thereof

-- 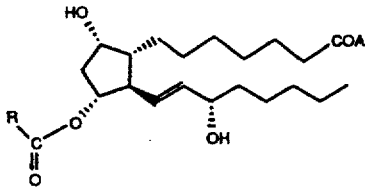 --

Column 3, line 45; delete "Preferred" and insert in place thereof --preferred--

Signed and Sealed this

Sixteenth Day of December, 1997

Attest:

BRUCE LEHMAN

Attesting Officer

Commissioner of Patents and Trademarks